(12) United States Patent
Guetta et al.

(10) Patent No.: US 7,397,552 B2
(45) Date of Patent: Jul. 8, 2008

(54) OPTICAL INSPECTION WITH ALTERNATING CONFIGURATIONS

(75) Inventors: Avishay Guetta, Rehovot (IL); Doron Korngut, Modiin (IL); Doron Shoham, Rehovot (IL); Iddo Pinkas, Rehovot (IL); Ronen Eynat, Shoham (IL)

(73) Assignee: Applied Materials, Israel, Ltd., Rehovot (IL)

( * ) Notice: Subject to any disclaimer, the term of this patent is extended or adjusted under 35 U.S.C. 154(b) by 215 days.

(21) Appl. No.: 11/234,492

(22) Filed: Sep. 22, 2005

(65) Prior Publication Data

US 2006/0066843 A1  Mar. 30, 2006

Related U.S. Application Data

(60) Provisional application No. 60/613,641, filed on Sep. 27, 2004.

(51) Int. Cl.
*G01N 21/00* (2006.01)
(52) U.S. Cl. .................. 356/237.2; 356/237.5
(58) Field of Classification Search ... 356/237.2–237.5; 382/144, 145
See application file for complete search history.

(56) References Cited

U.S. PATENT DOCUMENTS

| | | | |
|---|---|---|---|
| 4,191,476 A | 3/1980 | Pollard | |
| 4,643,381 A | 2/1987 | Levy | |
| 5,909,276 A | 6/1999 | Kinney et al. | |
| 6,249,381 B1 | 6/2001 | Suganuma | |
| 6,271,916 B1 | 8/2001 | Marxer et al. | |
| 6,366,690 B1 | 4/2002 | Smilansky et al. | |
| 6,392,793 B1 | 5/2002 | Chuang et al. | |
| 6,538,730 B2 | 3/2003 | Vaez-Iravani et al. | |
| 6,825,924 B2 | 11/2004 | Uda et al. | |
| 2002/0067478 A1* | 6/2002 | Karpol et al. ............ | 356/237.5 |
| 2003/0011760 A1* | 1/2003 | Vaez-Iravani et al. .... | 356/237.2 |
| 2004/0036865 A1* | 2/2004 | Isozaki et al. ............ | 356/237.3 |
| 2005/0002022 A1* | 1/2005 | Michelsson .............. | 356/237.5 |

* cited by examiner

*Primary Examiner*—Tarifur R Chowdhury
*Assistant Examiner*—Jonathon D Cook
(74) *Attorney, Agent, or Firm*—Tarek N. Fahmi

(57) ABSTRACT

An imaging system for inspection of a sample includes an illumination module, which irradiates a surface of the sample with pulsed optical radiation. A mechanical scanner translates at least one of the sample and part of the imaging system so as to scan an area irradiated by the pulsed optical radiation over the surface in order to irradiate successive, partially overlapping frames on the surface by respective successive pulses of the pulsed radiation. A collection module collects the optical radiation scattered from the surface so as to capture a sequence of images of the irradiated frames. A system controller varies a configuration of the imaging system in alternation between at least first and second different optical configurations in synchronization with the pulsed optical radiation.

20 Claims, 6 Drawing Sheets

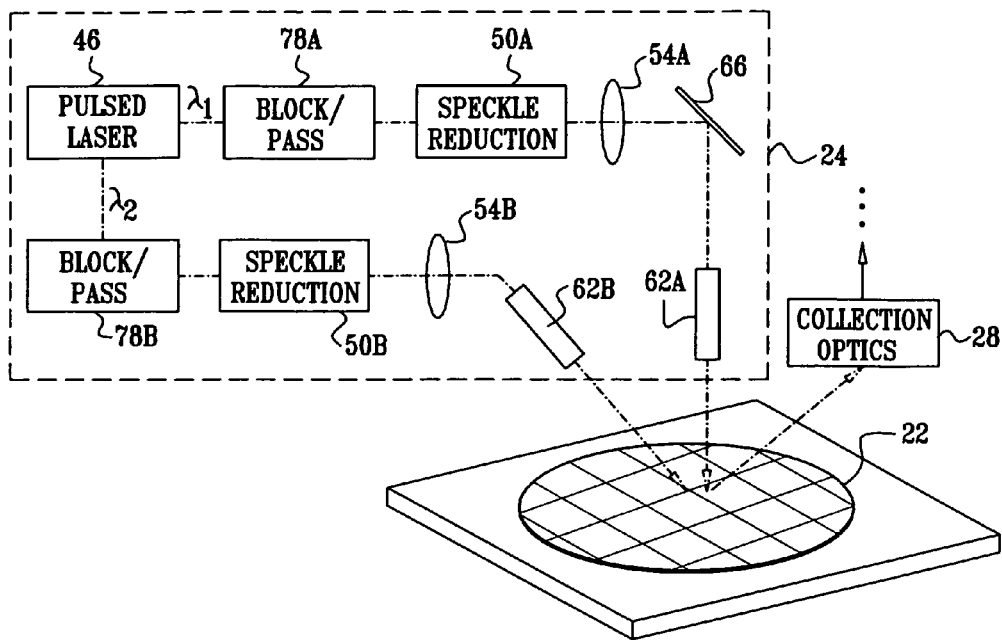
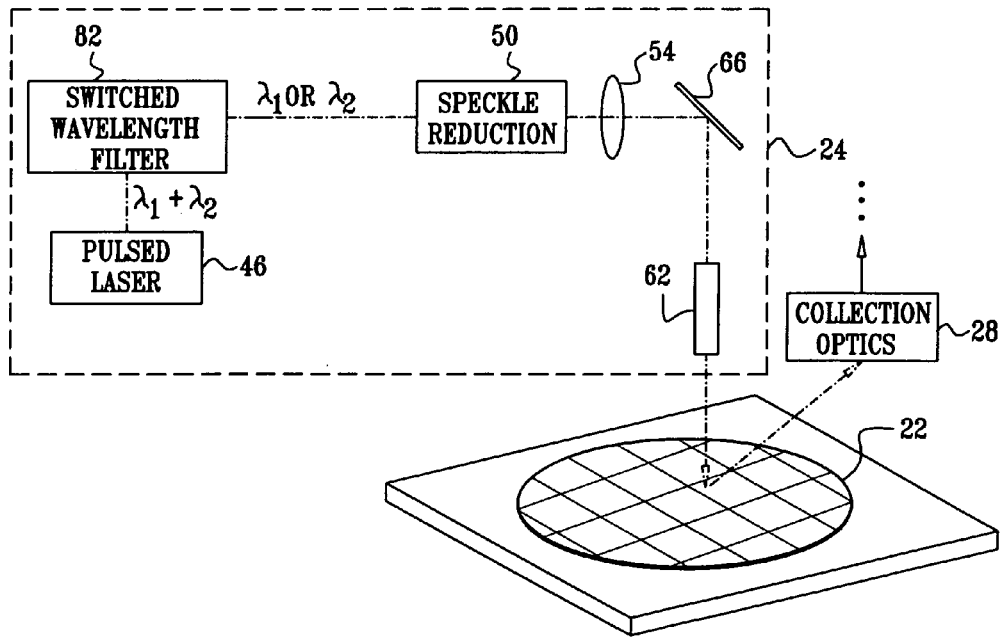

OPTICAL INSPECTION WITH ALTERNATING CONFIGURATIONS

CROSS-REFERENCE TO RELATED APPLICATION

This application claims the benefit of U.S. Provisional Patent Application 60/613,641, filed Sep. 27, 2004. This application is also related to U.S. patent application Ser. No. 10/511,092. Both of these related applications are incorporated herein by reference.

FIELD

The present invention relates generally to optical inspection, and particularly to methods and systems for detection of features and defects in semiconductor wafers.

BACKGROUND

Optical inspection is commonly used in semiconductor device manufacturing to detect defects on the surface of a wafer, such as contaminant particles, scratches and unremoved portions of material layers. Defects can cause device failures, thus substantially reducing the process yield. Therefore, careful inspection is required to verify the cleanliness and quality both of unpatterned wafers and of patterned wafers at various stages of the manufacturing process.

A common method for inspecting semiconductor wafers is to scan a laser beam over the wafer surface and measure the light scattered from each point on which the beam is incident. An exemplary inspection system, based on dark-field scattering detection, is described in U.S. patent application Ser. No. 10/511,092, cited above. Other optical inspection systems are described, for example, in U.S. Pat. Nos. 6,366,690, 6,271,916, 6,538,730, 6,392,793 and 5,909,276, whose disclosures are incorporated herein by reference.

In some applications, the optical inspection system uses two different light beams. For example, U.S. Pat. No. 4,191,476, whose disclosure is incorporated herein by reference, describes a system and method in which two patterns of illumination are formed independently on a photosensitive screen by means of light of two different wavelengths. The patterns are formed in the same manner, and each results from irradiation of the screen with light derived from a coherent source and consisting of two interfering beams, one of which is constituted by light scattered from the surface under inspection and imaged on to the screen. A video signal is derived from the screen representing the spatial variations in the sum of the intensities in the two patterns.

Another inspection system comprising dual-beam illumination is described in U.S. Pat. No. 6,825,924, whose disclosure is incorporated herein by reference. The system comprises an illuminator comprising a dual peak wavelength tube, which is a light source emitting two different colors of light. Each colored light has a narrow wavelength range, with a peak wavelength at a respective one of two complementary colors. The system comprises supporting means for supporting a substrate having a surface on which predetermined patterns are finely formed. The surface is illuminated at a predetermined angle with the light emanating from the illuminator, with the surface functioning as a diffraction grating. The system determines whether the pattern surface on the substrate is deformed due to defocusing as a result of said light being diffracted by the finely patterned surface.

U.S. Pat. No. 4,643,569, whose disclosure is incorporated herein by reference, describes a dual-beam laser inspection system comprising a scanner, which repetitively scans a line with first and second angularly displaced, synchronized scans. The system processes data received from each of the dual scanning beams in parallel, thereby reducing the data processing rate in comparison to a single-beam laser inspection apparatus operating at the same inspection rate.

SUMMARY OF THE INVENTION

Optical inspection systems are typically required to provide high defect detection capability, low false detection probability and a high throughput or speed. Such demanding requirements are sometimes limited by the hardware performance of the system. For example, one of the performance limitations associated with optical inspection systems is the limited dynamic range of the detector elements used for measuring the scattered radiation. In many practical cases, different features and components on the surface of the inspected sample have different scattering characteristics. As a result, the dynamic range of the scattered radiation often exceeds the dynamic range of the detector elements. The high dynamic range of the scattered radiation may cause some of the detector elements to saturate, and others to have poor signal to noise ratio. These effects significantly degrade the defect detection capability of the system.

Embodiments of the present invention provide improved methods and systems for optical inspection that overcome performance limitations such as those mentioned above. In some embodiments, an optical inspection system comprises an illumination module that irradiates the surface of the sample with pulsed optical radiation. The system scans the area irradiated by the pulsed optical radiation over the surface, thus irradiating a sequence of successive, partially-overlapping frames on the surface of the sample. Typically, successive frames are irradiated by respective successive pulses of the pulsed radiation. The system further comprises an optical collection module that collects the optical radiation scattered from the surface so as to capture a sequence of images of the irradiated frames.

In some embodiments, the system configuration is varied in alternation between two different optical configurations in synchronization with the pulsed optical radiation. As a result, the image sequence comprises two interleaved sub-sequences of images, each sub-sequence captured in one of the optical configurations. An image processor jointly processes the images in the first and second sub-sequences to detect defects in the sample.

The alternating optical configurations may differ from one another by their irradiation angle, numerical aperture, wavelength, polarization, or a combination of these parameters. In some embodiments, alternating the configuration of the imaging system may comprise alternating the configuration of the illumination module, the collection module, or both.

In some embodiments, the scanning pattern of the irradiated area, the pulse generation, the capturing of the images and the alternation between the two optical configurations are mutually synchronized so that each area of the sample surface is imaged at least once using each of the optical configurations. The imaging processor can then analyze features on the surface as imaged using the two configurations, to enhance the defect detection capability of the system.

Several exemplary optical configuration pairs are described herein, comprising different implementations of the illumination module and/or the collection module. Alternatively, the principles of the present invention may be applied in systems that alternate between three or more different optical configurations.

There is therefore provided, in accordance with an embodiment of the present invention, an imaging system for inspection of a sample, including:

an illumination module, which is arranged to irradiate a surface of the sample with pulsed optical radiation;

a mechanical scanner, which is arranged to translate at least one of the sample and part of the imaging system so as to scan an area irradiated by the pulsed optical radiation over the surface in order to irradiate successive, partially overlapping frames on the surface by respective successive pulses of the pulsed radiation;

a collection module, which is arranged to collect the optical radiation scattered from the surface so as to capture a sequence of images of the irradiated frames;

a system controller, which is arranged to vary a configuration of the imaging system in alternation between at least first and second different optical configurations in synchronization with the pulsed optical radiation, so that the sequence includes at least first and second alternating sub-sequences of the images that were captured respectively in the first and second optical configurations; and an image processor, which is arranged to jointly process the images in the first and second sub-sequences so as to detect a defect in the sample.

In an embodiment, the illumination module includes a pulsed laser, which is arranged to generate the pulsed optical radiation in at least one of an infra-red (IR), a visible light and an ultra-violet (UV) wavelength range.

In another embodiment, the mechanical scanner is arranged to perform at least one of translating the sample with respect to the illumination and collection modules and translating the illumination and collection modules with respect to the sample.

In yet another embodiment, the system controller is arranged to mutually synchronize a timing of the pulsed optical radiation, a scanning pattern of the mechanical scanner, a timing of capturing of the sequence of the images and a timing of alternating between the at least two optical configurations.

In still another embodiment, the illumination module includes a speckle reduction module, which is arranged to reduce a level of coherence-related speckles in the pulsed optical radiation prior to irradiating the surface.

In an embodiment, the illumination module includes first and second optical paths, which are arranged to irradiate the surface at respective different first and second irradiation angles corresponding to the respective first and second optical configurations, and a fast switching module (FSM) controlled by the system controller, the FSM arranged to alternately route the pulsed optical radiation to one of the first and second optical paths so as to vary the configuration of the imaging system.

In another embodiment, the illumination module includes a switchable shutter controlled by the system controller, the shutter arranged to alternate a numerical aperture of the pulsed optical radiation between two different values so as to vary the configuration of the imaging system.

In yet another embodiment, the illumination module includes a switchable polarizer/attenuator controlled by the system controller, the polarizer/attenuator arranged to alternate at least one of an intensity and a polarization of the pulsed optical radiation between two different values so as to vary the configuration of the imaging system.

In still another embodiment, the illumination module is arranged to alternate a wavelength of the pulsed optical radiation between two different values so as to vary the configuration of the imaging system.

In an embodiment, the collection module includes a switchable collection module controlled by the system controller, the switchable collection module arranged to alternate at least one of an angular range, a numerical aperture, an intensity and a polarization of at least some of the collected scattered radiation between two different values so as to vary the configuration of the imaging system.

Additionally or alternatively, the switchable collection module is arranged to simultaneously apply a first attenuation to the collected radiation scattered from a respective first area on the surface and a second attenuation, different from the first attenuation, to the collected radiation scattered from a respective second area on the surface.

In an embodiment, the collection module includes at least one detector array including multiple detector elements, which is arranged to image the collected scattered radiation so as to produce the sequence of images, and the system controller is arranged to alternate at least one of a gain and a sensitivity of at least some of the detector elements between two different values so as to vary the configuration of the imaging system.

There is additionally provided, in accordance with an embodiment of the present invention, a method for inspection of a sample using an imaging system, the method including:

irradiating a surface of the sample with pulsed optical radiation;

scanning an area irradiated by the pulsed optical radiation over the surface so as to irradiate successive, partially overlapping frames on the surface by respective successive pulses of the pulsed radiation;

collecting the optical radiation scattered from the surface so as to capture a sequence of images of the irradiated frames;

varying a configuration of the imaging system in alternation between at least first and second different optical configurations in synchronization with the pulsed optical radiation, so that the sequence includes at least first and second alternating sub-sequences of the images that were captured respectively in the first and second optical configurations; and jointly processing the images in the first and second sub-sequences to detect a defect in the sample.

BRIEF DESCRIPTION OF THE DRAWINGS

The present invention will be more fully understood from the following detailed description of the embodiments thereof, taken together with the drawings in which:

FIGS. 3-8 are block diagrams that schematically illustrate details of illumination modules, in accordance with embodiments of the present invention.

DETAILED DESCRIPTION OF EMBODIMENTS

System Description

Figure 1:
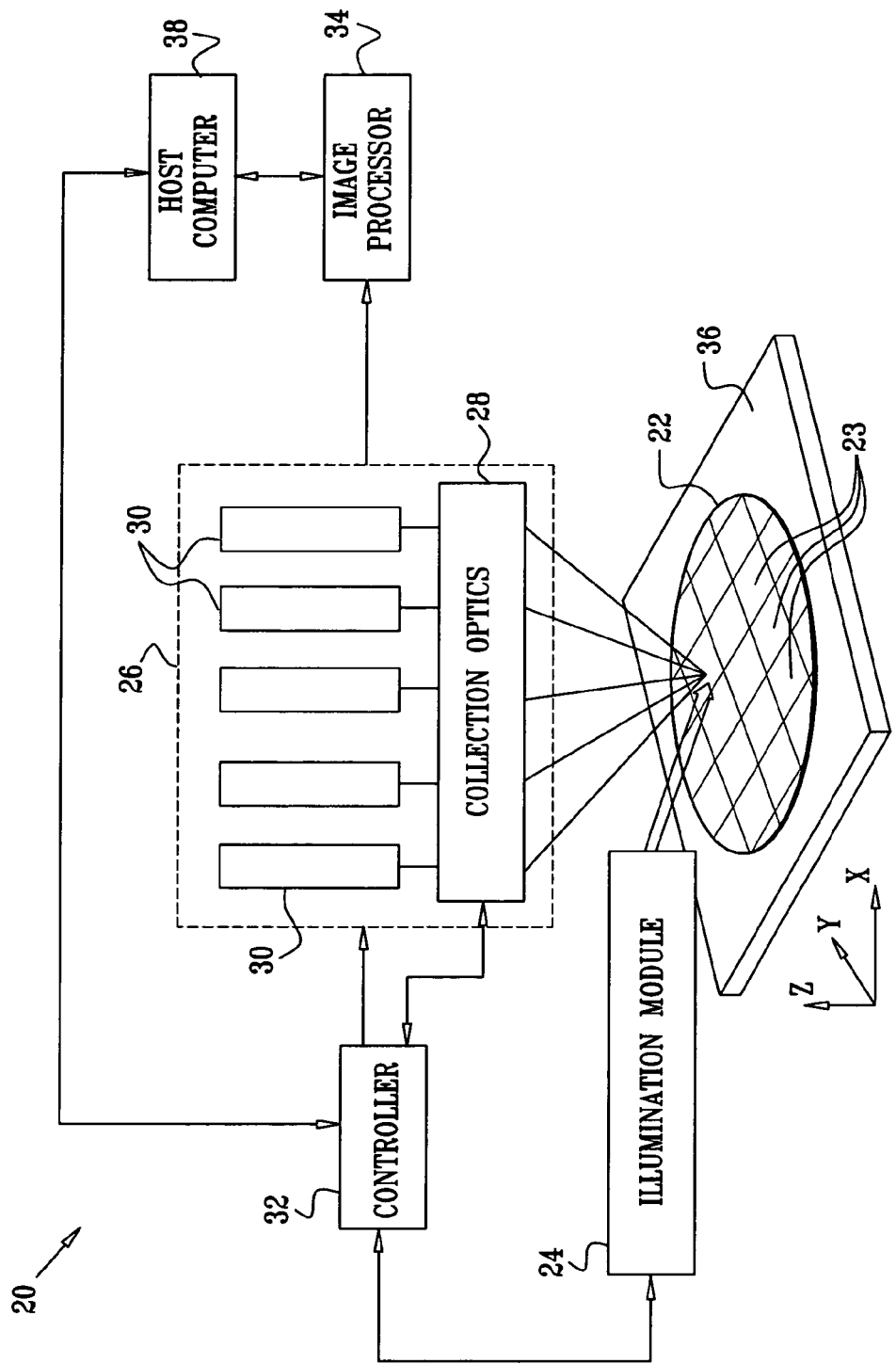
FIG. 1 is a block diagram that schematically illustrates a system for optical inspection, in accordance with an embodiment of the present invention.

FIG. 1 is a block diagram that schematically illustrates a system 20 for optical inspection of a sample, such as a semiconductor wafer 22, in accordance with an embodiment of the present invention. Typically, wafer 22 comprises multiple dies 23 of a particular semiconductor device arranged in a repetitive pattern. In some embodiments, wafer 22 is patterned, using any known semiconductor device fabrication process, and system 20 applies dark-field optical techniques to detect defects on the surface of the wafer. Alternatively, the principles of system 20 and the inspection methods described below may also be applied to unpatterned wafers and to inspection of other types of samples and surfaces, such as masks and reticles.

System 20 comprises an illumination module 24, which irradiates the surface of wafer 22. In some embodiments, module 24 comprises a light source, such as a laser, which emits pulsed laser radiation. In some embodiments, module 24 emits laser radiation at a single wavelength. In other embodiments, module 24 emits laser radiation at two or more different wavelengths, either simultaneously or one at a time. The laser radiation is directed by module 24 to impinge on wafer 22 either along a normal to the wafer surface or obliquely. The illumination module may be configured to emit optical radiation at wavelengths in the visible, ultraviolet (UV) and/or infrared (IR) ranges.

The radiation scattered from wafer 22 is collected over a predetermined range of angles by an optical collection module 26. Module 26 comprises collection optics 28, which image the surface of wafer 22 onto multiple cameras 30. Optics 28 may comprise either a single objective with high numerical aperture (NA) or a collection of individual objectives, one for each camera. Optics 28 and cameras 30 are arranged so that all the cameras image the same area on the wafer surface, i.e., the area illuminated by illumination module 24, while each camera captures the radiation that is scattered into a different angular range. Each camera 30 typically comprises a two-dimensional array of detector elements, such as a charge-coupled device (CCD) or a complementary metal oxide semiconductor (CMOS) array, as is known in the art. Each detector element of each of the arrays is imaged onto a corresponding spot within the area irradiated by illumination module 24. Thus, the scattering characteristics of any given spot on wafer 22 as a function of angle can be determined based on the signals generated by the corresponding detector elements in the different cameras 30.

Alternatively, in other embodiments of the present invention (not shown in the figures), collection module 26 may comprise only a single camera with appropriate optics. The principles of synchronization, alternating optical configuration and image processing that are described hereinbelow may be applied in this single-camera embodiment in substantially the same manner as the multi-camera embodiment shown in FIG. 1.

A system controller 32 synchronizes cameras 30 with the laser pulses generated by illumination module 24, so that each image generated by each camera corresponds to the radiation scattered from a single laser pulse. The output of each camera is received, digitized and analyzed by an image processor 34. The image processor often comprises dedicated hardware signal processing circuits and/or programmable digital signal processors (DSPs).

Figure 2:
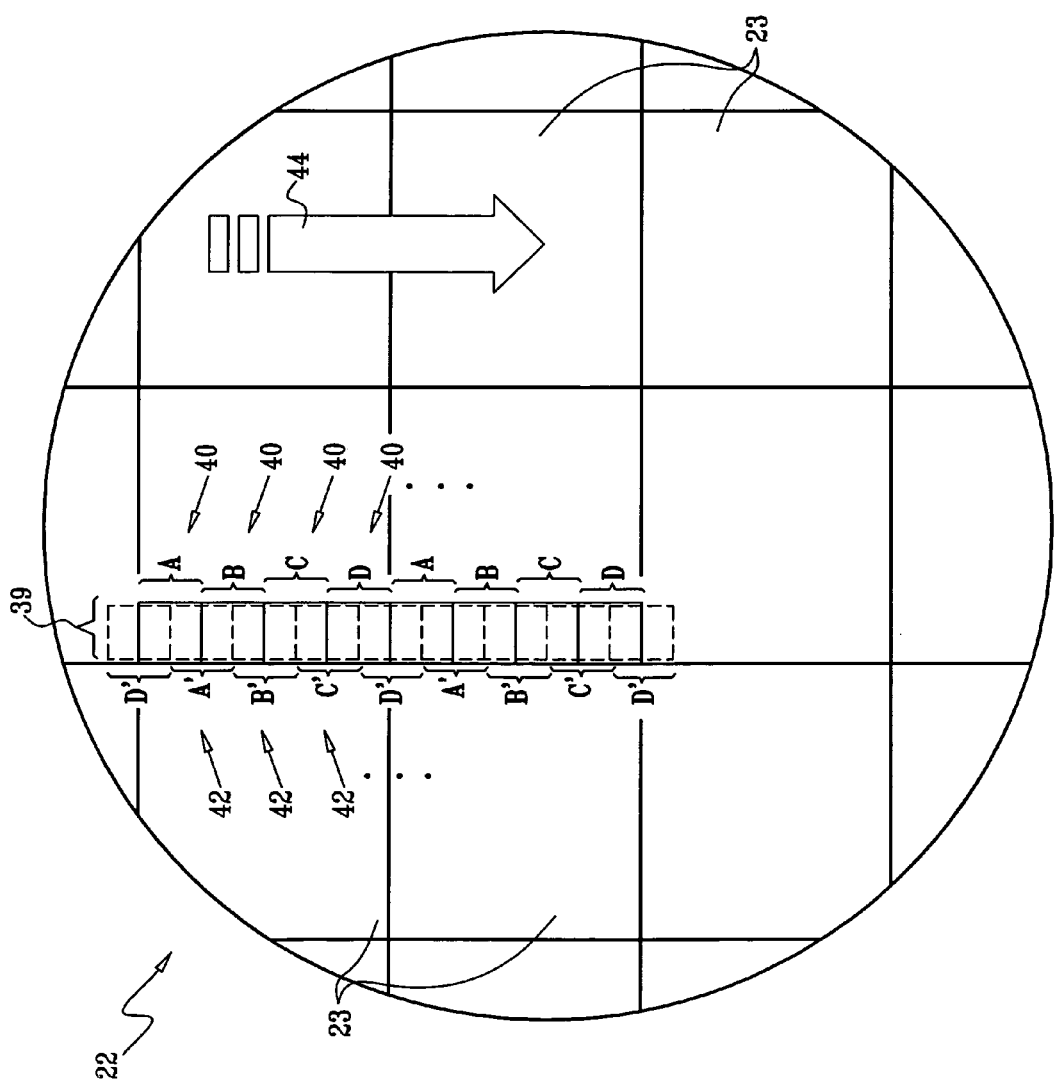
FIG. 2 is a schematic top view of a semiconductor wafer under inspection, in accordance with an embodiment of the present invention.

A mechanical scanner, such as an X-Y-Z stage 36, translates wafer 22, typically in a raster pattern, so that each laser pulse from illumination module 24 irradiates a different frame on the surface of the wafer, which typically overlaps the frame irradiated by the preceding pulse. An exemplary scanning pattern is shown in FIG. 2 below. In alternative embodiments, the wafer is held stationary and the illumination and collection modules are scanned relative to the wafer. The frame irradiated by module 24 and imaged by cameras 30 can be scanned using stage 36 over the entire wafer surface, or over a selected region thereof. If the pulses emitted by module 24 are sufficiently short, substantially less than 1 µs, for example, stage 36 may translate wafer 22 continuously in this manner without causing significant blur in the images captured by the cameras.

In some embodiments, system 20 images each area or feature on the surface of wafer 22 twice, using two different optical configurations, in order to use the dual imaging for detecting various surface defects. Typically, the system alternates between the two configurations at alternate laser pulses. Controller 32 synchronizes the mechanical translation of wafer 22 with the timing of the laser pulses, the image capture timing of cameras 30 and the alternation between the two optical configurations.

By using this synchronized operation, the system produces a sequence of images, one image captured with each laser pulse, of partially overlapping frames on the wafer surface. Since the system alternates between optical configurations with each laser pulse, the image sequence comprises two interleaved sub-sequences, each sub-sequence comprising images captured using one of the two optical configurations.

Image processor 34 processes the images produced by each of cameras 30 in order to extract image features that may be indicative of defects on the wafer surface. Processor 34 accepts from each camera 30 two sub-sequences of images of the irradiated surface, captured using the respective two optical configurations. Processor 34 jointly processes the images from the two sub-sequences to detect potential defects on the surface. The dual imaging process typically increases the probability of detecting defects and decreases the probability of false detections, as will be explained below. In some cases in which each of the optical configurations is sensitive to different types of defects, the number of detected defects will substantially double. In typical cases, however, there is an overlap between the defects imaged by each configuration. In such cases, in addition to increasing the detection probability of defects, the confidence level of identifying defects is increased as a result of the dual-configuration imaging.

In some embodiments, as part of the image processing, processor 34 registers images from the two sub-sequences to a common coordinate system, so that wafer features and components imaged in the two optical configurations can be correlated and compared.

In some embodiments, processor 34 selects from the two sub-sequences the image or images having the higher quality (e.g. the image having the higher resolution, higher contrast, or any other quality criterion) and uses this image to detect defects in the imaged area. Alternatively, processor 34 may combine information from both sub-sequences referring to a particular wafer feature or defect in order to improve the defect detection capability. Additionally or alternatively, processor 34 may analyze certain regions of the irradiated area using images from one of the sub-sequences and other regions using images from the second sub-sequence. In some embodiments, the decision as to which of the sub-sequences to use for each region or feature may be taken in accordance with a predefined map or other definition. In other embodiments, the decision may vary from image to image. Further additionally or alternatively, any suitable method, such as methods of pattern recognition and other image processing methods known in the art, may be used for identifying defects in the image sub-sequences.

The image features and/or potential identified defects are passed to a host computer 38, typically a general-purpose computer or workstation with suitable software. Computer 38 analyzes the features and generates a defect list or defect map with respect to the wafer under inspection.

The optical inspection system of FIG. 1 is an exemplary configuration, chosen for clarity and simplicity of explanation. Some aspects of this system are similar to an optical inspection system that is described in detail in U.S. patent application Ser. No. 10/511,092, cited above. The methods described below can alternatively be used in any suitable optical inspection or scanning system, including some of the systems described in the above-cited references.

Alternating Optical Configurations

As noted above, one of the performance limitations associated with optical inspection systems is the limited dynamic range of the detector elements in cameras 30. In many practical cases, different features on the surface of wafer 22 have different scattering characteristics. For example, die areas comprising memory devices are often characterized by repetitive, periodic patterns of conductors and components. This periodic structure typically reflects the majority of optical radiation in several discrete angles. A surface defect in such area of the die, however, often scatters the optical radiation more evenly over a wide angular range. Die areas comprising logic devices, on the other hand, typically scatter radiation over a wide angular range.

As a result of the different scattering properties across the die, the dynamic range of the scattered radiation imaged by cameras 30, in a particular optical configuration, often exceeds the dynamic range of the detector elements. In such cases, the images captured by cameras 30 often comprise areas in which the detector elements are saturated and/or areas of low intensity and poor signal-to-noise ratio, both significantly degrading the defect detection capability of the system.

In order to overcome the dynamic range limitation and to enhance the imaging quality and defect detection performance of system 20, the system images each feature on the surface of wafer 22 twice, using two different optical configurations. Optical configurations may differ from one another, for example, by their irradiation angle, numerical aperture, wavelength, polarization, or a combination of these parameters. FIGS. 3-9 below show several exemplary optical configuration pairs that can be used. Although some of the examples described herein are shown to overcome dynamic range limitations, the synchronized dual imaging methods generally provide improved detection performance in other imaging scenarios, as well. For example, some surface defects are easier to detect with a certain polarization or wavelength, regardless of the dynamic range.

As noted above, system 20 typically alternates between the two optical configurations with every laser pulse. In other words, even pulses use one of the configurations, while odd pulses use the other configuration. In some embodiments, the dual-configuration principle can be generalized, so that system 20 images wafer 22 using a larger number of optical configurations. In these embodiments, image processor 34 jointly processes a number of images equal to the number of optical configurations used.

FIG. 2 is a schematic top view of an exemplary semiconductor wafer 22 under inspection, in accordance with an embodiment of the present invention. Wafer 22 is divided into dies 23, with each die comprising a particular semiconductor device. In some embodiments, system 20 scans wafer 22 in a raster pattern, dividing the area of wafer 22 into multiple scan lines 39. At each laser pulse, illumination module 24 irradiates a particular frame on the surface of wafer 22. The mechanical translation of the wafer is synchronized with the laser pulses so that frames corresponding to successive laser pulses overlap one another along the scan line by approximately 50%.

FIG. 2 shows an exemplary scan line 39 made of an interleaved sequence of even frames 40 (denoted A, B, C, and D) corresponding to even laser pulses, and odd frames 42 (denoted A', B', C' and D') corresponding to odd laser pulses. As noted above, the even frames use one of the optical configurations, and the odd frames use the other configuration. The scan direction is indicated by an arrow 44. In this example, system 20 sequentially irradiates the frames denoted A, A', B, B', C, C', D, D', A, A', . . . on the wafer surface. Consequently, cameras 30 capture a sequence of images corresponding to this sequence of frames.

It can be seen from the figure that each point on the surface of wafer 22 is imaged twice, once with an even frame and once with an odd frame. As a result, image processor 34 receives from each camera 30 the two image sub-sequences [A, B, C, D, A, B, . . . ] and [A', B', C', D', A', B', . . . ], each captured using one of the two different optical configurations. Because of the 50% overlap between successive frames in the sequence, system 20 uses a double laser pulse rate, in comparison with an inspection system that uses only a single optical configuration and operates at the same scanning speed.

In many cases, all dies 23 of wafer 22 are duplications of a particular surface pattern. Furthermore, many defect detection methods are based on die-to-die comparisons, or on a comparison of an imaged die to a "gold standard" die. For these reasons, the frames are typically labeled with respect to their position within die 23. (For example, frame A in FIG. 2 always denotes the top left corner frame of the die.) Frame boundaries are often aligned with the die boundaries. The methods and systems described herein can be carried out regardless of the presence or absence of any repetitive pattern, such as die duplication, on the wafer surface. Similarly, the methods and systems described herein can be implemented given any numbering or labeling of dies and any alignment or misalignment of frame boundaries with die boundaries.

The scanning pattern shown in FIG. 2 is an exemplary pattern chosen for clarity of explanation. In alternative embodiments, wafer 22 can be scanned using any number of scan lines and frames. Overlap ratios different from 50% can also be used. In particular, the overlap may be increased slightly to ensure that areas close to frame boundaries are not missed due to scanning tolerances or other edge effects. For the same reason, a slight overlap may be introduced between successive even frames and between successive odd frames. Any suitable scanning pattern other than the raster pattern shown in FIG. 2 can also be used. Frame boundaries may be either aligned or asynchronous with die boundaries.

Exemplary Optical Configuration Pairs

Figure 3:
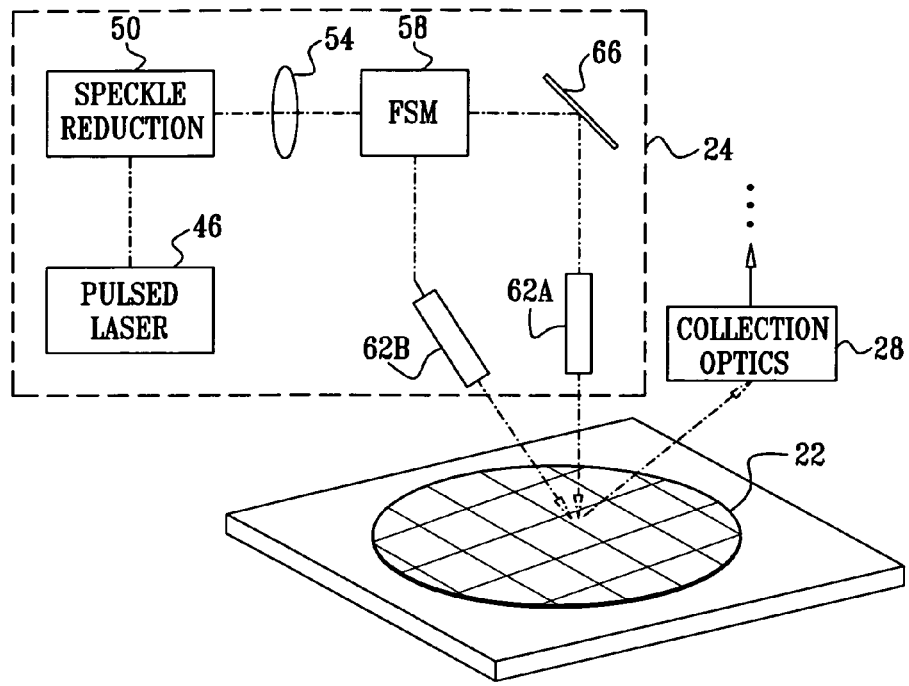

FIG. 3 is a block diagram that schematically illustrates details of illumination module 24, in accordance with an embodiment of the present invention. In FIG. 3, module 24 alternately irradiates wafer 22 at two different irradiation angles. A laser 46 in module 24 emits a train of laser pulses. The pulse rate of laser 46 is typically in the range of 0.1-20 KHz and the pulse duration is typically in the range of 6-1000 ns, although other suitable values can also be used.

In some embodiments, the laser pulses are processed by a speckle reduction module 50 in order to reduce the speckles that normally arise due to the coherence of the laser radiation. Speckle is a well-known effect in imaging systems that use coherent illumination, caused by die strong amplitude auto-correlation of the laser. Speckle reduction techniques are known in the art. Some techniques involve passing the laser beam through a rotating diffuser that reduces the amplitude autocorrelation. Other techniques involve passing the beam through one or more bundles of optical fibers of different lengths. Speckle reduction methods are described, for example, in the above-cited U.S. patent application Ser. No. 10/511,092, and in U.S. Pat. No. 6,249,381 and U.S. Patent Application Publication US 2002/0067478 A1, whose disclosures are incorporated herein by reference. Any suitable speckle reduction technique can be used for implementing module 50.

The laser pulses are passed through a lens 54 into a fast switching module (FSM) 58. FSM 58 alternately routes the laser pulses at its input to one of two outputs, thus alternating between two different optical paths, each comprising illumination optics 62. In the example of FIG. 3, the first optical path, comprising illumination optics 62A, irradiates wafer 22 at a normal angle. The second optical path, comprising illumination optics 62B, irradiates wafer 22 at an oblique angle. Alternatively, any two irradiation angles different from one another can be chosen. One or more mirrors 66 may be used in either optical path in order to appropriately direct the laser radiation.

In some embodiments, FSM 58 comprises a suitable acousto-optic deflection (AOD) device. An exemplary device that can be used for this purpose is a 4080-2 acousto-optic deflector, produced by Crystal Technology, Inc. (Palo Alto, Calif.). Details regarding this device are available at www.crystaltechnology.com/acoustoopticdefl.html. Alternatively, FSM 58 may comprise a suitable spatial light modulator (SLM), such as liquid crystal-based devices produced by Meadowlark Optics (Frederick, Colo.). Details regarding these products are available at www.meadowlark.com/Products/SLM.htm. Alternatively, FSM 58 may comprise a suitable micro-electro-mechanical system (MEMS), such as the 0.7XGA micromirror device produced by the Digital Light Processing (DLP™) division of Texas Instruments, Inc. (Plano, Tex.). Details regarding this product are available at www.dlp.com. Further alternatively, FSM 58 may comprise any other suitable device capable of alternately routing the laser pulses to illumination optics 62A and 62B at the desired switching rate.

Illumination optics 62A and 62B each comprise a suitable cascade of lenses, filters, and/or other optical components for focusing and directing the laser pulses to irradiate the desired spot size on wafer 22 at the desired intensity and irradiation angle.

Collection optics 28 collect the radiation scattered from the surface of wafer 22. From this point, the imaging and defect detection process continues in accordance with the system description of FIGS. 1 and 2 above.

Figure 4:
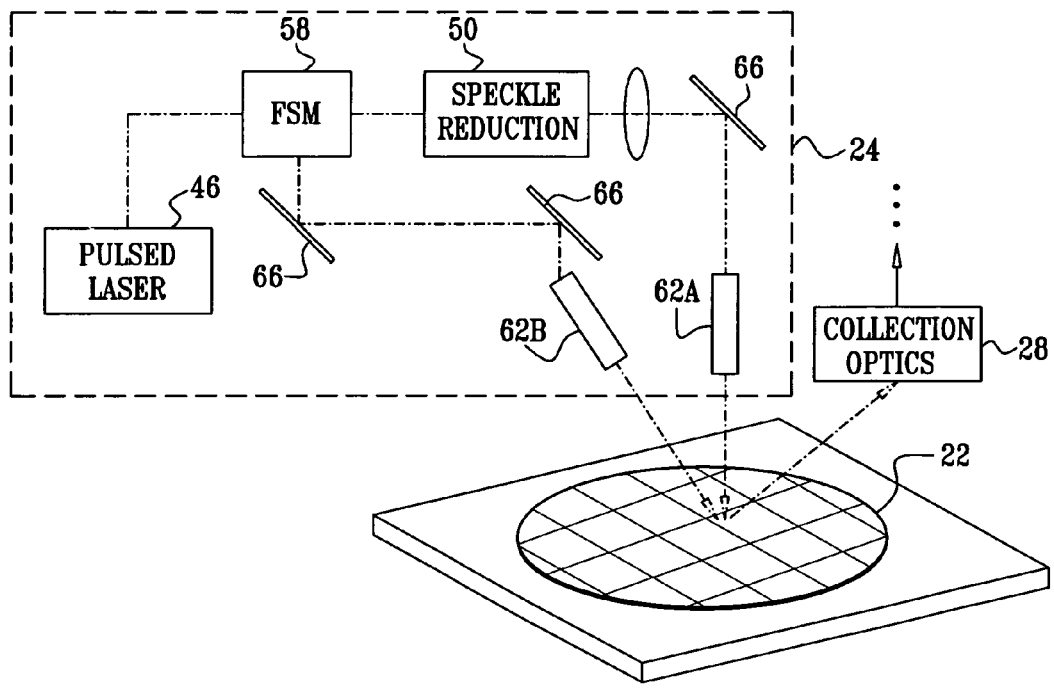

FIG. 4 is a block diagram that schematically illustrates details of illumination module 24, in accordance with another embodiment of the present invention. FIG. 4 is another example of using two optical configurations having different irradiation angles. In the present example, however, FSM 58 is positioned before speckle reduction module 50, and module 50 is included in only one of the optical configurations. Thus, the alternate routing of laser pulses to illumination optics 62A and 62B is performed prior to speckle reduction. This configuration is useful, for example, for having illumination optics 62B irradiate wafer 22 with higher intensity and/or lower numerical aperture (NA). Illumination optics 62A, on the other hand, irradiates wafer 22 with lower intensity (because of the inherent transmission loss of speckle reduction module 50) and/or higher numerical aperture.

Figure 5:
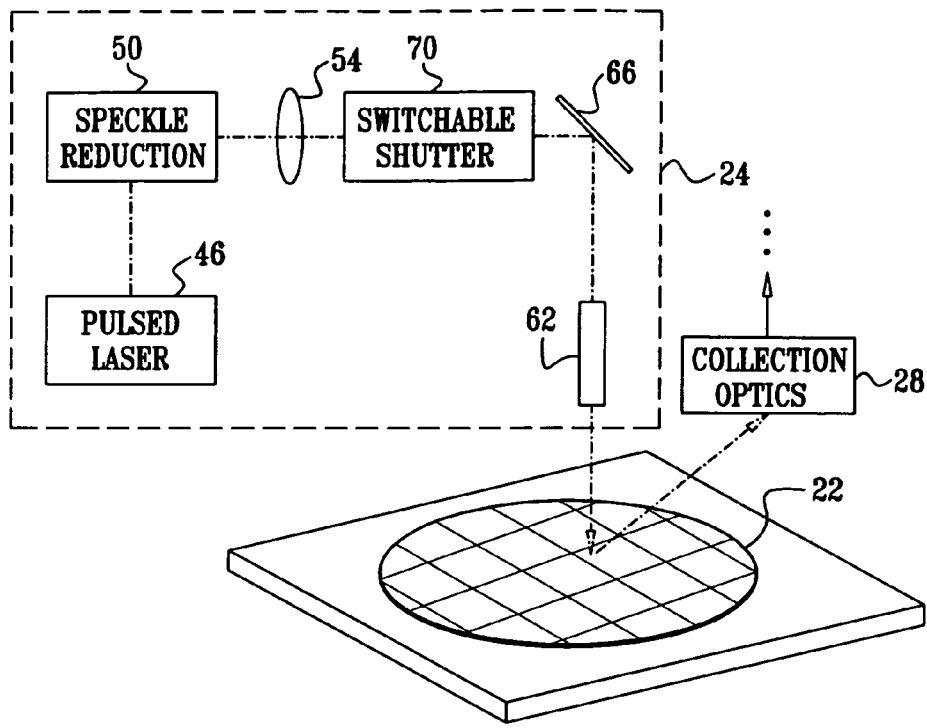

FIG. 5 is a block diagram that schematically illustrates details of illumination module 24, in accordance with yet another embodiment of the present invention. In FIG. 5, two optical configurations having different numerical apertures are implemented in a single optical path by using a switchable shutter 70. The diameter of shutter 70 is alternated between two predetermined values in synchronization with the laser pulses, thus providing two optical configurations having different numerical apertures. The shutter diameter switching is controlled by controller 32, and is typically synchronized with the timing of cameras 30 and with the scanning pattern of the system. For example, shutter 70 may comprise an electromechanical shutter such as Uniblitz® devices produced by Vincent Associates (Rochester, N.Y.). Details regarding these devices are available at www.uniblitz.com. Although illumination optics 62 is shown in the figure as irradiating the wafer at a normal angle, any suitable irradiation angle can be used.

Figure 6:
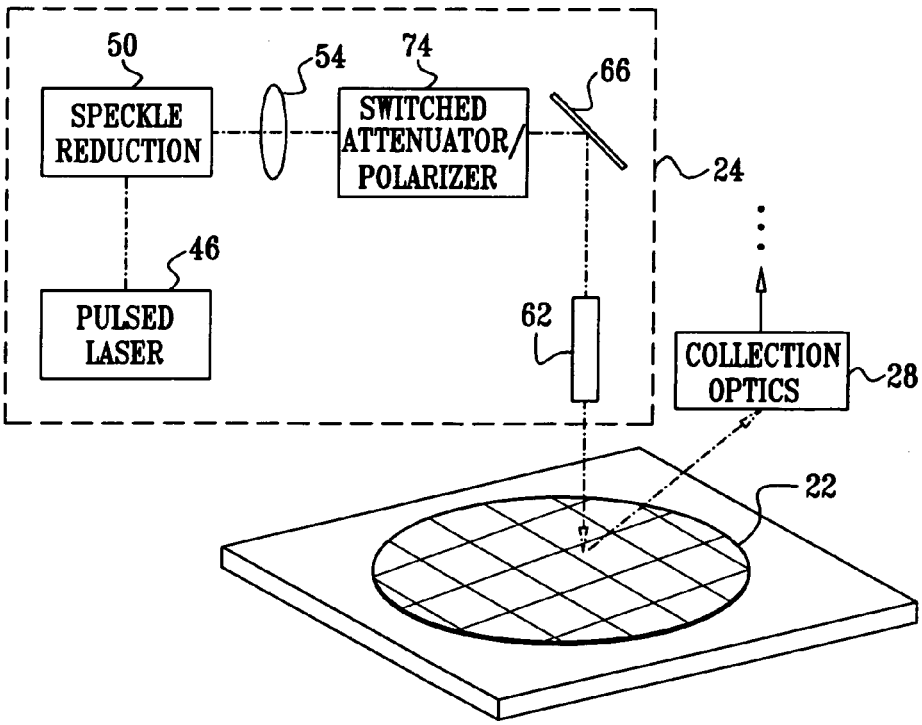

FIG. 6 is a block diagram that schematically illustrates details of illumination module 24, in accordance with still another embodiment of the present invention. FIG. 6 also uses a single optical path. A switched attenuator/polarizer 74 alternates the intensity and/or polarization of the laser pulses between the two optical configurations.

Optical configurations having different polarizations are useful, for example, for imaging die areas comprising dense periodic conductor patterns, such as memory areas and buses. Such periodic structures cause strong reflections when the polarization of the incident radiation is parallel to the orientation of the conductors, and weak reflections when the polarization is perpendicular with respect to the conductor orientation.

Optical configurations having different intensities are useful in a variety of high dynamic range scenarios. Out of the two images provided to image processor 34, the image captured using the higher intensity configuration is typically used to examine die areas that produce weak reflections. The second image, captured using the lower intensity configuration, is used to analyze areas of strong reflections, which are often saturated in the first image.

Attenuator/polarizer 74 is controlled and synchronized by controller 32. In some embodiments, attenuator/polarizer 74 comprises a Pockels cell device, such as the PBC05 device produced by Inrad, Inc. (Northvale, N.J.). Details regarding this device are available at www.inrad.com/pages/crystals.html. In some embodiments, alternating the beam intensity can be performed by coupling a switched polarization modulator to a fixed polarizer, as is known in the art. As in FIG. 5 above, illumination optics 62 can be arranged in any suitable irradiation angle.

FIG. 7 is a block diagram that schematically illustrates details of illumination module 24, in accordance with another embodiment of the present invention. In the present example, the two optical configurations use different optical wavelengths and irradiation angles. Laser 46 here comprises a dual-wavelength laser that simultaneously emits pulses having two wavelengths denoted $\lambda_1$ and $\lambda_2$ into two respective optical paths. A pair of block/pass modules 78, denoted 78A and 78B, are alternately controlled by controller 32 so that one of them passes the odd pulses and blocks the even pulses, and vice versa. In some embodiments, block/pass modules 78 may comprise a suitable MEMS device, such as the Texas Instruments DLP devices described above, which controllably deflects every second pulse away from the optical path into a suitable dumper device. Alternatively, the block/pass modules may comprise a suitable switchable shutter, such as shutter 70 described above, which is alternately switched between an open setting and a fully-closed setting.

The pulses in the first and second optical paths pass through speckle reduction modules 50A and 50B, lenses 54A and 54B and illumination optics 62A and 62B, respectively, before irradiating the surface of wafer 22. This configuration is useful, for example, in cases where different die areas react differently to different wavelengths. As another example, dual-wavelength imaging can be useful when the wafer has a top layer that is transparent to one of the two wavelengths used. By using two wavelengths, defects can be detected both above and below this layer.

FIG. 8 is a block diagram that schematically illustrates details of illumination module 24, in accordance with yet another embodiment of the present invention. In FIG. 8, the two optical configurations use different optical wavelengths at the same irradiation angle, using a single optical path. Laser 46 comprises a dual-wavelength laser emitting pulses at wavelengths $\lambda_1$ and $\lambda_2$. A switched wavelength filter 82 is controlled by controller 32 so as to pass wavelength $\lambda_1$ at even pulse intervals while blocking wavelength $\lambda_2$. At odd pulse intervals, filter 82 is controlled so as to pass wavelength $\lambda_2$ while blocking wavelength $\lambda_1$. For example, switched wavelength filter 82 may comprise a quartz acousto-optic device, such as a model 4390 produced by Crystal Technology, Inc. (Palo Alto, Calif.).

The output of filter 82 thus comprises a train of pulses whose wavelength alternates between $\lambda_1$ and $\lambda_2$ from pulse to pulse. The pulses pass through speckle reduction module 50, lens 54, mirror 66 and illumination optics 62 before irradiating wafer 22. Although FIG. 8 shows optics 62 as irradiating the wafer at a normal angle, any suitable irradiation angle can be used.

FIGS. 3-8 above show exemplary embodiments in which the alternation between the two optical configurations is performed in illumination module 24. Additionally or alternatively, the alternation between optical configurations can be performed in collection module 26. Such exemplary embodiments are explained in the description of FIG. 9 below. Other embodiments of system 20 can be implemented using any suitable combination of the configurations of FIGS. 3-9, as well as additional optical configuration pairs, which will be apparent to those skilled in the art after reading the description of these embodiments.

Figure 9:
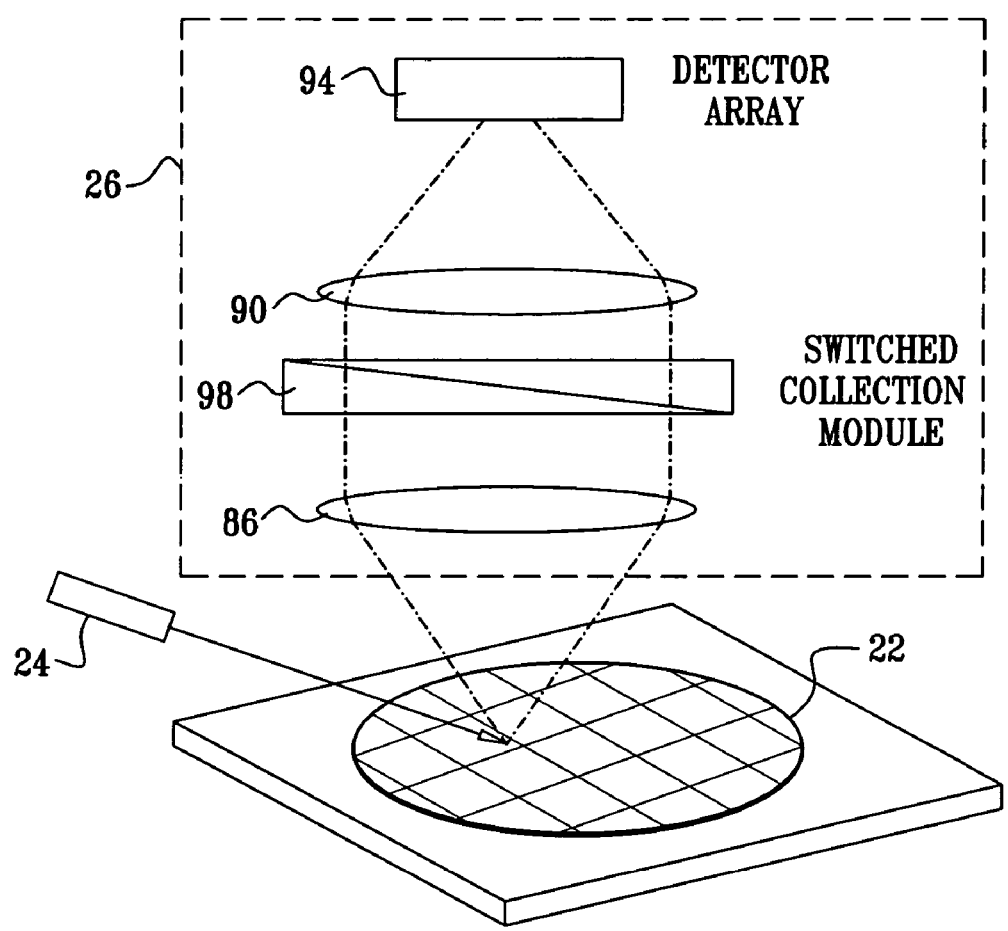
FIG. 9 is a block diagram that schematically illustrates details of a collection module, in accordance with an embodiment of the present invention.

FIG. 9 is a block diagram that schematically illustrates details of collection module 26, in accordance with an embodiment of the present invention. In this embodiment, illumination module 24 irradiates wafer 22 at a predetermined angle, which can be either normal or oblique. The scattered radiation is collected by an objective lens 86. An imaging lens 90 focuses the scattered radiation onto the plane of a detector array 94 of camera 30. A switched collection module 98 is positioned in the optical path between lenses 86 and 90. Module 98 is controlled by controller 32 so as to alternate the optical collection properties of module 26 between two predetermined configurations from one laser pulse to another.

In some embodiments, module 98 comprises a fast switching module similar to FSM 58 of FIGS. 3 and 4 above. Module 98 thus changes the angular range of radiation collected by module 26. Similar to FSM 58, in some embodiments module 98 may comprise an acousto-optic device, an SLM or a MEMS device, as explained above.

In other embodiments, module 98 may comprise a suitable polarization rotator, such as the MEMS devices (DLP) or liquid crystal-based devices (Meadowlark) cited above, for alternating the polarization of the collected radiation.

In still other embodiments, module 98 may comprise a suitable variable transmission device, such as a Kerr cell, as is known in the art, which alternates between two predetermined transmission values so as to alternate the intensity (dynamic range) of the collected radiation.

Additionally or alternatively, alternating the dynamic range of the collected radiation can be performed by alternating the gain and/or sensitivity of the detector elements in detector array 94.

In some embodiments, module 98 may comprise a mask that provides non-uniform attenuation across the angular range of radiation collection. For example, in cases in which certain areas of the die or wafer are expected to produce stronger reflections, module 98 may be used to block or attenuate scattered radiation from these areas, thereby preventing detector saturation and degradation. In such embodiments, objective lens 86 and module 98 are set so that module 98 is positioned in the image plane of the inspected wafer surface, and lens 90 images the plane of module 98 onto the plane of detector array 94. In some embodiments, the blocked and/or attenuated areas can be identified and set in module 98 prior to the inspection process as an external, predetermined mapping. In other embodiments, these areas can be automatically or semi-automatically identified at an initial learning phase that maps high reflection areas on the wafer surface.

In an alternative embodiment, module 98 can perform alternating spatial filtering of the collected radiation. In this embodiment, collection optics 28 alternate between two different ranges of collection angles.

Although the methods and systems described herein mainly address dark-field inspection of semiconductor wafers, aspects of the present invention may also be applied in bright-field inspection, as well as in other areas of illumination, inspection and imaging such as the inspection of reticles, liquid crystal displays (LCD) and printed circuit boards (PCB).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

We claim:

1. An imaging system for inspection of a sample, comprising:

an illumination module, arranged to irradiate a surface of the sample with pulsed optical radiation;

a mechanical scanner, arranged to translate at least one of the sample and a part of the imaging system to scan an area of the surface irradiated by the pulsed optical radiation and to irradiate a first frame and a plurality of successive, substantially overlapping frames on the surface by respective successive pulses of the pulsed radiation, each said successive frame having an overlap with a respective preceding frame of at least 50%;

a collection module, arranged to collect the optical radiation scattered from the surface so as to capture a sequence of images of the first frame and the plurality of successive, substantially overlapping frames;

a system controller, arranged to vary a configuration of the imaging system in alternation between at least a first configuration and a second, different, configuration, said alternation being synchronized with the pulsed optical radiation, whereby the sequence of images comprises at least a first set of images captured in the first optical configuration and a second set of images captured in the second optical configuration, and whereby at least two images of at least a portion of the area of the surface are captured, said at least two images comprising a first image captured using the first optical configuration and a second image captured using the second optical configuration; and an image processor, arranged to jointly process the first image and the second image to detect a defect in the sample by analyzing features on the surface as imaged using each of the first and the second optical configurations.

2. The system according to claim 1, wherein the illumination module comprises a pulsed laser, which is arranged to generate the pulsed optical radiation in at least one of an infra-red (IR), a visible light and an ultraviolet (UV) wavelength range.

3. The system according to claim 1, wherein the mechanical scanner is arranged to perform at least one of translating the sample with respect to the illumination and collection modules and translating the illumination and collection modules with respect to the sample.

4. The system according to claim 1, wherein the system controller is arranged to mutually synchronize a timing of the pulsed optical radiation, a scanning pattern of the mechanical scanner, a timing of capturing of the sequence of the images and a timing of alternating between the at least two optical configurations.

5. The system according to claim 1, wherein the illumination module comprises a speckle reduction module, which is arranged to reduce a level of coherence-related speckles in the pulsed Optical radiation prior to irradiating the surface.

6. The system according to claim 1, wherein the illumination module comprises first and second optical paths, which are arranged to irradiate the surface at respective different first and second irradiation angles corresponding to the respective first and second optical configurations, and a fast switching module (FSM) controlled by the system controller, the FSM arranged to alternately route the pulsed optical radiation to one of the first and second optical paths so as to vary the configuration of the imaging system.

7. The system according to claim 1, wherein the illumination module comprises a switchable shutter controlled by the system controller, the shutter arranged to alternate a numerical aperture of the pulsed optical radiation between two different values so as to vary the configuration of the imaging system.

8. The system according to claim 1, wherein the illumination module comprises a switchable polarizer/attenuator controlled by the system controller, the polarizer/attenuator arranged to alternate at least one of an intensity and a polarization of the pulsed optical radiation between two different values so as to vary the configuration of the imaging system.

9. The system according to claim 1, wherein the illumination module is arranged to alternate a wavelength of the pulsed optical radiation between two different values so as to vary the configuration of the imaging system.

10. The system according to claim 1, wherein the collection module comprises a switchable collection module controlled by the system controller, the switchable collection module arranged to alternate at least one of an angular range, a numerical aperture, an intensity and a polarization of at least some of the collected scattered radiation between two different values so as to vary the configuration of the imaging system.

11. The system according to claim 10, wherein the switchable collection module is arranged to simultaneously apply a first attenuation to the collected radiation scattered from a respective first area oil the surface and a second attenuation, different from the first attenuation, to the collected radiation scattered from a respective second area on the surface.

12. The system according to claim 1, wherein the collection module comprises at least one detector array comprising multiple detector elements, which is arranged to image the collected scattered radiation so as to produce the sequence of images, and wherein the system controller is arranged to alternate at least one of a gain and a sensitivity of at least some of the detector elements between two different values so as to vary the configuration of the imaging system.

13. A method for inspection of a sample using an imaging system, the method comprising:

irradiating a surface of the sample with pulsed optical radiation;

scanning an area of the surface irradiated by the pulsed optical radiation and irradiating a first frame and a plurality of successive, substantially overlapping frames on the surface by respective successive pulses of the pulsed radiation, each said successive frame having an overlap with a respective preceding frame of at least 50%;

collecting the optical radiation scattered from the surface so as to capture a sequence of images of the first frame and the plurality of successive, substantially overlapping frames;

varying a configuration of the imaging system in alternation between at least a first configuration and a second, different, configuration, said alternation being synchronized with the pulsed optical radiation, whereby the sequence of images comprises at least a first set of images captured in the first optical configuration and a second set of images captured in the second optical configuration, and whereby at least two images of at least a portion of the area of the surface are captured, said at least two images comprising a first image captured using the first optical configuration and a second image captured using the second optical configuration; and jointly processing the first image and the second image to detect a defect in the sample by analyzing features on the surface as imaged using each of the first and the second optical configurations.

14. The method according to claim 13, wherein irradiating the surface comprises generating the pulsed optical radiation using a pulsed laser operating in at least one of an infra-red (IR), a visible light and an ultraviolet (UV) wavelength range.

15. The method according to claim 13, wherein scanning the area comprises at least one of translating the sample with respect to the pulsed optical radiation and translating the pulsed optical radiation with respect to the sample.

16. The method according to claim 13, wherein irradiating the surface, scanning the area, collecting the radiation and varying the configuration comprise mutually synchronizing a timing of the pulsed optical radiation, a scanning pattern of the sample with respect to the pulsed optical radiation, a timing of capturing of the sequence of the images and a timing of alternating between the at least two optical configurations.

17. The method according to claim 13, wherein irradiating the surface comprises reducing a level of coherence-related speckles in the pulsed optical radiation.

18. The method according to claim 13, wherein varying the configuration of the imaging system comprises alternating at least one of an irradiation angle of the irradiated pulsed radiation, a collection angle of the collected radiation, a numerical aperture of the irradiated pulsed radiation, a numerical aperture of the collected radiation, a polarization of the irradiated pulsed radiation, a polarization of the collected radiation, an intensity of the irradiated pulsed radiation, an intensity of the collected radiation and a wavelength of the irradiated pulsed radiation between two different values.

19. The method according to claim 13, wherein collecting the optical radiation comprises imaging the scattered radiation using at least one detector array comprising multiple detector elements so as to produce the sequence of images, and wherein varying the configuration of the imaging system comprises alternating at least one of a gain and a sensitivity of at least some of the detector elements between two different values.

20. The method according to claim 13, wherein collecting the optical radiation comprises simultaneously applying a first attenuation to the collected radiation scattered from a respective first area on the surface and a second attenuation, different from the first attenuation, to the collected radiation scattered from a respective second area on the surface.

\* \* \* \* \*